United States Patent [19]

Kaplan

[11] 4,154,770
[45] May 15, 1979

[54] ISOPARAFFIN-OLEFIN ALKYLATION UTILIZING A MEMBRANE TO SEPARATE OLEFINS FROM A FEED STREAM

[75] Inventor: Richard D. Kaplan, Wheaton, Ill.

[73] Assignee: Standard Oil Company (Indiana), Chicago, Ill.

[21] Appl. No.: 919,861

[22] Filed: Jun. 28, 1978

[51] Int. Cl.² ............................................. C07C 3/52
[52] U.S. Cl. .................................... 585/332; 585/717; 585/818; 585/844; 585/809
[58] Field of Search ............... 260/683.43, 683.49, 260/683.61, 683.47, 683.58, 677 A

[56] References Cited

U.S. PATENT DOCUMENTS

| | | | |
|---|---|---|---|
| 3,078,321 | 2/1963 | Van Pool et al. | 260/683.49 |
| 3,370,102 | 2/1968 | Carpenter et al. | 260/683.62 |
| 3,758,603 | 9/1973 | Steigelmann et al. | 260/677 A |
| 3,773,844 | 11/1973 | Perry et al. | 260/677 A |
| 3,864,418 | 2/1975 | Hughes et al. | 260/677 A |
| 4,014,665 | 3/1977 | Steigelmann | 260/677 A |
| 4,060,566 | 11/1977 | Yahnke | 260/677 A |

*Primary Examiner*—George Crasanakis
*Attorney, Agent, or Firm*—Thomas J. Connelly; Arthur G. Gilkes; William T. McClain

[57] ABSTRACT

This invention relates to an improved process for the alkylation of olefins in an alkylation unit feed stream in order to produce a higher yield of alkylate having a higher octane number, a lower acid consumption rate, and a lower energy consumption. Such a process involves passing a feed stream comprised of olefins and paraffins through a membrane so that the olefins are separated from the paraffins. In passing through the membrane, the olefins are facilitated in their transport by an isoparaffin sweep stream and together, the olefin/isoparaffin stream is passed into an alkylation reactor. Within the reactor, the olefins react with the isoparaffins to form alkylate.

15 Claims, No Drawings

ISOPARAFFIN-OLEFIN ALKYLATION UTILIZING A MEMBRANE TO SEPARATE OLEFINS FROM A FEED STREAM

BACKGROUND OF THE INVENTION

1. Field of the Invention

This invention relates to an improved process for the alkylation of olefins in an alkylation unit feed stream with a view to producing a higher yield of alkylate having a higher octane number, a lower acid consumption rate, and a lower energy consumption. This improved process comprises the steps of passing a feed stream comprised of olefins and paraffins through a membrane whereby the olefins and paraffins are separated into an olefin stream, comprised of olefins, and a paraffin stream, comprised of normal paraffins and isoparaffins. An isoparaffin sweep stream is used to facilitate transport of the olefins across the membrane and the resulting olefin/isoparaffin stream is then passed into an alkylation reactor. Within the reactor, the olefins react with the isoparaffins to form alkylate.

2. Description of the Prior Art

Alkylation is a process which is widely practiced in the petroleum refining industry to produce liquid gasoline from normally gaseous hydrocarbons. It involves the reaction of low molecular weight isoparaffins, such as isobutane with low molecular weight olefins such as ethylene, propylene, butylenes and pentenes (amylenes). A particularly advantageous process is one in which isobutane is reacted with butylenes. As conventionally practiced, the alkylation process is usually conducted at low temperatures in the presence of a strong mineral acid catalyst, e.g., about 40° F. for sulfuric acid and about 90° F. for hydrofluoric acid. The manner of conducting the process and the conditions at which optimum results are obtained are all well known to those skilled in the art. Ordinarily, the feed to the process is a mixture of light hydrocarbons such as that produced in a catalytic cracker or other refining operations and this feed usually contains varying amounts of n-paraffins, isoparaffins, and olefins. In addition, since the catalytic cracker feed to the unit does not ordinarily contain the amount of isoparaffins required to alkylate all the olefins in this stream, other streams from various refinery and outside sources, containing isobutane and normal butane, are also fed to the unit. However, such mixtures are not the most desirable feed to an alkylation unit in view of the n-paraffin content since it is only the isoparaffins which will catalytically alkylate. The n-paraffins do not react and serve merely as diluents in the reaction mixture.

Since best results are obtained when the isoparaffins are present in a substantial molal excess as compared to the olefins, economics dictate that the unreacted isoparaffins should be separated from the alkylate and be recycled back to the reactor. As mentioned earlier, an alkylation feed stream will ordinarily contain non-reactive n-paraffins as well as reactive isoparaffins. Consequently, the n-paraffins must be separated from the isoparaffins before the latter are recycled to the alkylation reactor since, otherwise, the n-paraffins would tend to accumulate and diminsh the efficiency of the reactor. In the n-butane-isobutane situation, separation is difficult because of the close proximity of the boiling points of the compounds and, up until now, it has been necessary to resort to expensive distillation equipment to accomplish this separation. Furthermore, a perfect separation between the normal and isoparaffins has been totally impractical with conventional distillation equipment and consequently a substantial quantity of the n-paraffins are circulated within the alkylation unit. The presence of the n-paraffins necessitates the treatment of larger streams by the deisobutanizer and the depropanizer which in turn results in a greater energy consumption. Difficult separations are also encountered when one tries to remove the n-paraffins from an ethane-ethylene feed, a propane-propylene feed, or a pentane-pentene feed. Accordingly, there is a need for a process that provides a method of separating the olefins from the paraffins, and facilitating the transport of the olefins by an isoparaffin sweep stream so that a higher yield of alkylate can be produced with a lower acid consumption rate, and a lower energy consumption.

Commonly assigned U.S. Pat. Nos. 3,758,603, 3,758,605 and 4,060,566 disclose membrane separation of olefins from paraffins where the membranes are capable of separating both liquids and gases. For best results, a permeable film membrane made of cellulose triacetate impregnated with silver nitrate is used. Generally, a sweep stream is used to facilitate transport of the olefins through the membrane.

Accordingly, it is the general object of this invention to provide an improved process for the alkylation of an olefin feed stream. More specifically, the object of this invention is to reduce the concentration of n-paraffins in the alkylation reactor so that a higher alkylate yield is possible with lower energy consumption.

Another object of this invention is to provide an improved process which will produce an alkylate having a higher octane number.

Still another object of this invention is to provide an improved process which has a lower acid consumption rate.

Still further, an object of this invention is to provide an improved process for the alkylation of olefins in an alkylation unit feed stream when the feed stream contains ethane-ethylene, propane-propylene, butane-butylene, pentane-pentene, or combinations thereof.

We have now found that the objects of this invention can be attained by passing a feed stream comprised of olefins and paraffins through a membrane whereby the olefins are separated from the paraffins into an olefin stream comprised of olefins, and a paraffin stream comprised of normal paraffins and isoparaffins. The olefins are facilitated in their transport across the membrane by a separate isoparaffin sweep stream and this combined olefin/isoparaffin stream is passed into an alkylation reactor wherein the olefins react with the isoparaffin to form alkylate. This process has the additional advantage of being physically incorporated into existing alkylation units with a minimal amount of engineering changes.

SUMMARY OF THE INVENTION

Briefly this invention provides an improved process for the alkylation of olefins in an alkylation unit feed stream containing a variety of hydrocarbons including olefins, n-paraffins and isoparaffins, in order to produce a higher yield of alkylate having a higher octane number, a lower acid consumption rate and a lower energy consumption. Such a process involves passing a feed stream comprised of olefins and paraffins through a membrane whereby two separate streams are formed, an olefin stream, comprised of olefins, and a paraffin stream, comprised of normal paraffins and isoparaffins. The olefin stream is facilitated in its transport across the membrane by an isoparaffin sweep stream and this resulting olefin/isoparaffin stream is passed into an alkylation reactor. Within the reactor, the olefins react with the isoparaffins to form alkylate.

It is contemplated that the olefin-paraffin separation can occur in either the liquid or gaseous phase. In addition, it is also possible to pass the paraffin stream, containing n-paraffins and isoparaffins, through a second separation zone to facilitate the separation of the isoparaffins from the n-paraffins. The isoparaffins would then be routed into either the alkylation reactor wherein they would react with the olefins to form alkylate or be used to facilitate transport of the olefins across a membrane while the n-paraffins would be disposed of, for example, for further separation, blending or heating purposes. In such a process, the second separation zone could be any one of several different devices, such as: a membrane, a molecular sieve membrane, molecular sieves, or activated charcoal. It is also possible to substitute an isomerization unit for the second separation zone and thereby convert a significant portion of the n-paraffins to isoparaffins.

The removal of n-paraffins from an alkylation unit feed stream will result in numerous benefits. It has been found that the removal of paraffins from a feed stream that also contains olefins, for example: an ethane-ethylene feed, a propane-propylene feed, a butane-butylene feed, or a pentane-pentene feed is particularly advantageous. The advantages inherent in removing the n-paraffins from the olefin containing feed, rather than after reaction, are two-fold. First, such a process provides an alkylate having a higher octane number, a lower acid consumption rate and a higher alkylation yield. This result is possible due to the higher isobutane concentration in the reactor which results from the removal of the diluents (n-paraffins). The second advantage is that either the size of the stream which has to be treated is reduced, or the number of treatment units which have to be employed are reduced and this results in a significant energy saving.

DETAILED DESCRIPTION OF THE INVENTION

By the improved process of this invention n-paraffins are removed from an alkylation unit feed stream when a sulfuric acid catalyst, a hydrofluoric acid catalyst, or an aluminum chloride catalyst is present. In such an improved process, an alkylation unit feed stream, containing both olefins and paraffins is direction through a membrane separation device whereby the olefins are separated from the paraffins. In passing through the membrane, the olefins are facilitated in their transport by an isoparaffin sweep stream and together, the olefin-/isoparaffin stream is passed into an alkylation reactor wherein the components react to form alkylate.

Adsorption is a process in which a solid material is used to remove one or more components from a liquid or gas stream without chemical reaction. Just as certain liquids have different affinities for different hydrocarbons, so also do certain solids. If a liquid or gas hydrocarbon mixture is contacted with such a solid, certain of its components will concentrate on the surface; this effect makes separation possible. Since adsorption is a surface phenomenon, usually only one molecule deep, an adsorbent must be highly porous, a typical surface area being about 700 m²/g. In the adsorption of liquid, only small particles may be used because larger particles (larger than about 14 mesh in the case of silica-alumina) tend to fracture in a cyclic adsorption operation. Most adsorbents can be utilized for separation purposes because they have different affinities for different types of hydrocarbons, such as aromatics, olefins, naphthalenes, paraffins, etc. Some examples of practical adsorbents are: silica gels, silica-aluminas, activated aluminas and activated charcoals. Silica-aluminas have had wide acceptance because they have a low tendency to fracture in adsorption operations. Also, activated carbon is being increasingly used, for it has the greatest adsorbent capacity and therefore is very useful in separating light hydrocarbons.

Another class of adsorbents are molecular sieves, which facilitate the separation of gaseous (vapor) or liquid mixtures by two mechanisms: adsorption, whereby they have a strong preference for polar components such as water, hydrogen sulfide and carbon dioxide; and separation by size, whereby only those molecules are retained which fit into the pore openings of the sieve. For example, a molecular sieve with an average pore diameter of 4 Å will adsorb ethane but pass propane.

A normal separation process using molecular sieves is frequently based on a cyclic operation. Here, the gas or liquid is passed through a bed of molecular sieves, usually at ambient temperature and high partial pressure. After the adsorbent has been saturated to a point just below that where the undesirable component (normal butane for example) would break through, the adsorbent is taken off stream and regenerated by heating and purging with a carrier gas, commonly nitrogen or fuel gas. At the completion of the regeneration period, the adsorbent bed is cooled and returned to the process.

A permeable or semi-permeable film membrane made of cellulose triacetate impregnated with silver nitrate or cuprous ions as the complexing medium is preferred. It can be constructed in fiber form and should be kept wet by water so as to be capable of retaining the metal ion on it. This condition is easily satisfied since feed streams to an alkylation reactor contain saturation water, which will keep the membrane moist. Preferably, the membrane should be capable of separating both liquids and gases (vapors), although the liquid stream will be the one most frequently encountered. The film membranes described by Steigelmann et al. in U.S. Pat. Nos. 3,758,603 and 3,758,605 and Yahnke, U.S. Pat. No. 4,060,566 are incorporated by reference and made a part hereof.

U.S. Pat. No. 3,758,603 describes the separation of aliphatically-unsaturated hydrocarbons from mixtures by the combined use of liquid barrier permeation and metal complexing techniques. The liquid barrier is in contact with a film membrane and the barrier contains complex-forming metal ions in aqueous solution.

U.S. Pat. No. 3,758,605 relates to the separation of aliphatically-unsaturated hydrocarbons by the combined use of liquid barrier permeation and metal complexing techniques wherein the liquid barrier containing complex-forming metal ions is within a hydrophilic semi-permeable membrane.

U.S. Pat. No. 4,060,566 relates to a process for separating components, e.g., olefinically-unsaturated hydrocarbons, from mixtures with other materials by liquid barrier permeation and metal-complexing techniques using a semi-permeable membrane and a partial pressure differential across the membrane for the material being separated. This process also mentions using a sweep liquid in downstream processing of the separated material, either as a reactant, or as a solvent. However, the Yahnke patent does not teach or suggest the use of an isoparaffin as a sweep liquid and the subsequent passing of this olefin/isoparaffin stream to an alkylation reactor for reaction therein to form an alkylate.

When the olefins and paraffins come into contact with the membrane the olefins complex with the silver nitrate and pass through it while the paraffins are rejected. The olefins are then facilitated in their transport across and away from the membrane by an isoparaffin sweep stream which passes by the opposite side of the membrane. The sweep stream maintains an olefin partial pressure differential across the membrane so that olefin permeation is maximized. The olefins along with the isoparaffin sweep liquid, preferably isobutane, are routed into the alkylation reactor wherein the olefins react with isoparaffins to form alkylate. The two most common isoparaffins which are available for reacting with the olefins to form alkylate are isobutane and isopentane. The former is preferred. The remaining paraffin-rich stream, containing normal paraffins and isoparaffins, which are prevented from passing through the membrane is routed either to a storage tank for subsequent use, such as for further separation, blending or heating purposes, or it can be disposed of.

Another embodiment of this invention concerns the treatment of the paraffin-rich stream along with other saturated paraffin streams from various refinery locations when two separation zones are present. These streams can come, for example, from a coker, a reformer or a hydrocracker and they usually contain propane, isobutane and normal butane. Together, these paraffin streams enter the second separation zone wherein the isoparaffins are separated from the n-paraffins. The separation zone can consist of any suitable separation means, for example: a membrane, a molecular sieve, a molecular sieve membrane, activated carbon, or any other satisfactory type of membrane. Preferably, a membrane is used for the second separation zone because of its low energy consumption and minimal maintenance problems. Just as in the first separation step, the second separation zone can be conducted in either the liquid or vapor phase, and this is true regardless of the type of phase employed in the first step. It is also feasible to substitute a conversion means, such as an isomerization unit, into the second separation zone so that a significant portion (greater than 50%) of the n-paraffins is converted to isoparaffins.

The isoparaffin-rich stream, containing the separated isoparaffins or the converted isoparaffins depending upon whether a separation or conversion means was employed in the second separation zone, passes into the alkylation reactor wherein the isoparaffins react with the olefin to form alkylate. The alkylation system can consist of various designs or configurations but will contain: a reactor, a settler—from which acid is recycled, a refrigeration system and a product separation system. Various types of reactors and refrigeration systems can be used to practice this invention. As for a refrigeration system, most reactors contain either an open or closed loop refrigerant cycle which has the capability of controlling the reaction temperature within the alkylation reactor. The settler and refrigeration components are considered standard equipment to an alkylation unit and their specific location is not considered essential to the novel feature of this invention. As for the alkylation unit itself, any type of commercial unit presently available is sufficient. The most frequent types of sulfuric acid alkylation units are: Stratco with effluent refrigeration or closed loop refrigeration, Cascade-auto refrigeration with turbine mixers or emulsion pump circulators, jet reactor or time tank. When a hydrofluoric acid catalyst unit is desired, the alkylation reactor could be of the Phillips Universal Oil Products or other HF design. When an aluminum chloride catalyst is present, one can use a Phillips or a Shell unit.

Within the alkylation reactor the olefins react with the isoparaffins, which are in excess, to form alkylate. This alkylate, along with excess isoparaffins, is passed to a deisobutanizer (hereinafter referred to as a DIB) wherein the alkylate is separated out and recovered. The alkylate contains branched chain hydrocarbons which are beneficial in producing high antiknock fuels. The isoparaffins on the other hand, containing essentially isobutane, exit the DIB as overhead and are recycled back to the reactor for further reaction with incoming olefins. A portion of this isoparaffin stream is used as the sweep streams which flows past the olefin-paraffin separation membrane and facilitates the transport of the olefins through the membrane and into the reactor.

The normal paraffin-rich stream containing the separated n-paraffins which were unable to pass through the second separation zone are routed to a depropanizer so that the propane can be separated from the heavier n-paraffins. The propane is recovered as overhead and can be sold commercially as propane gas, LPG or be rerouted to other refinery operations for various uses, for example, propane deasphalting. The n-paraffins, consisting essentially of normal butane, exit the depropanizer as bottoms and can be subsequently used for gasoline blending, or for heating purposes.

In certain situations it may be beneficial to locate the depropanizer between the olefin-paraffin separation membrane and the second separation zone. In such an arrangement the depropanizer separates the propane from the paraffins before the isoparaffin-normal paraffin separation. This arrangement eliminates the propane which would normally have to be handled by the second separation zone and is especially advantageous when a large quantity of propane is present. The remaining sequence of steps is the same as enunciated above.

Another advantage of this improved process is its ability to conserve energy. Although there are a number of ways to conserve energy in an alkylation unit by sacrificing octane, there are very few techniques available for saving energy, as well as concomitantly improving octane number. By removing n-paraffins (normal butane in particular) from an alkylation unit feed stream, one can save energy by improving the separation efficiency of the deisobutanizer (DIB), which is a major energy consumer in an alkylation unit. Additional energy can also be saved by allowing the debutanizer to be shut down and by reducing the volume of the stream which the depropanizer has to handle. This technique can improve alkylate octane by reducing the concentration of diluents in the reactor (i.e., by effectively raising reactor isobutane concentration), as well as reducing acid consumption and increasing alkylate yield. In the prior art, there are several patents which deal with a technique similar to that stated above. Two of these patents are: U.S. Pat. No. 2,946,832 issued to W. L. Vermilion, Jr., entitled "Alkylation Process" and U.S. Pat. No. 3,105,102 issued to O. Webb, Jr., entitled "Alkylation Process With Normal Paraffin Removal." The Vermilion patent describes the use of molecular sieves to remove normal butane from the DIB overhead, which is one of the major components of an alkylation unit. The Webb patent teaches the use of 5 Å molecular sieves to remove n-paraffins from the hydrocarbon settler effluent or DIB feed. However, neither of these patents deal with olefin containing feeds.

A careful search of the prior art also revealed that only U.S. Pat. No. 3,052,743 issued to Beavon, relates to n-paraffin removal from olefin containing alkylation unit streams. The Beavon patent does consider treating the olefin feed, but in a manner inferior to that described herein by Applicant. In Beavon, the olefin stream is contacted with 92% sulfuric acid in the absence of excess isobutane to form alkyl sulfates. A separator is then used to remove saturated paraffins from the acid containing the alkyl sulfates. The acid is then fed to the reactor, while polymers, n-paraffins, and acidic materials are removed from the saturate stream before it is recycled to the reactor as an essentially pure isobutane stream. This approach is subordinate to the process of this invention in that some polymerization occurs when the olefin is contacted with the sulfuric acid in the absence of excess isobutane. This results in a poorer quality alkylate, a higher acid consumption, and a decreased alkylate yield. In comparison with a normal unit, it is evident that such additional equipment as: a cooled contacting vessel, a separator, a caustic wash tank, a water wash drum, a distillation column (to reject polymer), and molecular sieve beds are required. Another drawback is that any high molecular weight sulfates formed upon contacting the olefins with acid will be soluble in the hydrocarbon phase and could cause increased downstream corrosion.

While the invention is described in connection with the specific examples below, it is to be understood that these are for illustrative purposes only and should not be construed as limiting the scope of this invention.

EXAMPLE 1

This example illustrates the improved process of this invention whereby n-paraffins are removed from an alkylation unit feed stream when a sulfuric acid catalyst is present. A calculation simulating the process of this invention was performed under the assumption of complete recovery of the olefins, in the liquid state, through a film membrane made of cellulose triacetate impregnated with silver nitrate. The composition of the various streams is calculated in barrels per standard day. The feed stream is comprised of 50 barrels of propane 270 barrels of isobutane, 150 barrels of normal butane, 30 barrels of isopentane, 25 barrels of propene, and 475 barrels of butene. This feed stream is directed through the membrane wherein the olefins (25 barrels of propene and 475 barrels of butene) are able to pass through while the paraffins (50 barrels of propane, 270 barrels of isobutene, 150 barrels of normal butane and 30 barrels of isopentane) are prevented from doing so. The olefin stream (25 barrels of propane and 475 barrels of butene) is assisted across the membrane by an isoparaffin sweep stream which consist of a portion of an isoparaffin recycle stream from a deisobutanizer located downstream of the alkylation reactor. Together, this olefin/isoparaffin stream is passed into the alkylation reactor wherein the olefins react with the isoparaffins to form alkylate. Meanwhile, the paraffin stream (50 barrels of propane, 270 barrels of isobutane, 150 barrels of normal butane and 30 barrels of isopentane) which is unable to pass through the membrane is passed to a second separation zone along with saturated paraffins (370 barrels of isobutane and 50 barrels of normal butane) from various refinery locations. In this second separation zone, the isoparaffins are separated from the n-paraffins by means of a membrane into an isoparaffin stream and a n-paraffin stream. The n-paraffin stream (200 barrels of normal butane and 50 barrels of propane) is passed into a depropanizer wherein the propane is separated from the heavier n-paraffins. The propane (50 barrels) is then recovered as overhead and the n-paraffins (200 barrels of normal butane) are recovered as bottoms to be disposed of as seen fit.

The isoparaffin stream leaving the second separation zone (640 barrels of isobutane and 30 barrels of isopentane) is passed directly to the alkylation reactor. Within the alkylation reactor the olefins react with the isoparaffins to form alkylate (1,072 barrels of pentane and alkylate) and this alkylate along with excess isoparaffins (1,876 barrels of isobutane), is passed to a deisobutanizer wherein the alkylate is separated from the isoparaffins. The alkylate (892 barrels), which is beneficial in producing high anti-knock fuels, is recovered as final product from the bottom of the deisobutanizer. The remaining isoparaffins, containing essentially isobutane (1,800 barrels of isobutane and 180 barrels of alkylate) passes as overhead from the deisobutanizer and is recycled back to the alkylation reactor for further reaction with incoming olefins. A portion of this stream is used as the sweep stream which flows past the first membrane and facilitates the transport of the olefins across it.

EXAMPLE 2

This example illustrates the improved process of this invention whereby n-paraffins are removed from an alkylation unit feed stream when a hydrofluoric acid catalyst is present. A calculation simulating the process of this invention was performed under the assumption of complete recovery of the olefins, in the liquid state, through a film membrane made of cellulose triacetate impregnated with silver nitrate. The composition of the various streams is calculated in barrels per standard day. The feed stream is comprised of 50 barrels of propane, 270 barrels of isobutane, 150 barrels of normal butane, 30 barrels of isopentane, 25 barrels of propene and 475 barrels of butene. This feed stream is directed through the membrane wherein the olefins (25 barrels of propene and 475 barrels of butene) are able to pass through while the paraffins (50 barrels of propane, 270 barrels of isobutane, 150 barrels of normal butane and 30 barrels of isopentane) are prevented from doing so. The olefin stream (25 barrels of propene and 475 barrels of butene) is assisted across the membrane by an isoparaffin sweep stream which consisted of a portion of an isoparaffin recycle stream from a deisobutanizer located downstream of the alkylation reactor. Together, this olefin-/isoparaffin stream is passed into the alkylation reactor wherein the olefins react with the isoparaffins to form alkylate. Meanwhile, the paraffin stream (50 barrels of propane, 270 barrels of isobutane, 150 barrels of normal butane and 30 barrels of isopentane) which is unable to pass through the membrane is passed to a depropanizer wherein the propane (50 barrels) and hydrofluoric acid, (2 barrels) which is recycled to the depropanizer from an isostripper, are recovered as overhead. This propane and hydrofluoric acid are then routed to a receiver, which is similar to a large settling tank, where a major portion of the hydrofluoric acid is recovered and reused. The propane along with the remaining portion of hydrofluoric acid is passed into an HF stripper in which the propane is separated from the hydrofluoric acid and is recovered. The small amount of hydrofluoric acid recovered from the HF stripper as overhead is reused in the system.

The remaining paraffins (50 barrels of propane, 270 barrels of isobutane, 150 barrels of normal butane, 30 barrels of isopentane and 66 barrels of alkylate) are passed from the depropanizer to a second separation zone where they join other saturated paraffins (390 barrels of isobutane and 55 barrels of normal butane) from various refinery locations. Note that the 66 barrels of alkylate which is present in the bottom stream of the depropanizer is originally part of the recycle stream from an isostripper located downstream of the alkylation reactor, and this alkylate is recycled to the top portion of the depropanizer. In the second separation zone the isoparaffins (1,020 barrels of isobutane and 66 barrels of alkylate) are separated from the n-paraffins (210 barrels of normal butane) and then passed into the alkylation reactor. The remaining n-paraffins (210 barrels of normal butane) are removed from the second separation zone and disposed of.

In the hydrofluoric acid catalyst alkylation unit the olefins react with the isoparaffins to form alkylate (1,072 barrels) in the presence of hydrofluoric acid. This fresh hydrofluoric acid (10 barrels) is furnished to the alkylation reactor by an input stream in order to replace the quantity which is lost. The alkylate (1,072 barrels) along with excess isoparaffins (1,875 barrels of isobutane) and a small amount of propane (25 barrels) and hydrofluoric acid (10 barrels) are passed to an isostripper wherein the alkylate is separated from the isoparaffins. As isostripper which is substituted for a DIB performs essentially the same function as a deisobutanizer except with less energy consumption, and this apparatus is particularly desirable when a hydrofluoric acid catalyst is present. A major portion of the alkylate (892 barrels) is recovered from the bottom of the isostripper as the final product while the overhead, consisting of isoparaffins (1,800 barrels of isobutane), hydrofluoric acid (10 barrels), propane (25 barrels), normal butane (28 barrels) and alkylate (180 barrels) is recycled upstream to the alkylation reactor and the depropanizer. The overhead stream is split by conventional means so that a substantial portion of the isoparaffins (1,440 barrels) and hydrofluoric acid (8 barrels) are recycled to the alkylation reactor. The remainder of the overhead stream goes to the top portion of the depropanizer, wherein the propane and hydrofluoric acid are separated from the n-paraffins. A portion of the overhead stream is used as the sweep stream which flows past the first membrane separation device and facilitates transport of the olefins across it.

It should be noted that the depropanizer is located downstream from the isostripper because some of the hydrofluoric acid will catalyze the reaction of the olefin within the alkylation reactor to form additional propane. Therefore, it is economically feasible to build only one depropanizer situated downstream from the reaction zone instead of having to construct two such depropanizers, one upstream of the reactor and one downstream from it. Also, when the depropanizer is situated downstream from the isostripper it has a smaller stream to handle and this results in an energy saving. It is likewise beneficial to retain a means for removing the n-paraffins from the isostripper, and this can be accomplished either by having a debutanizer located downstream from the isostripper or by taking a n-paraffin side draw from the isostripper.

I claim:

1. A process for the alkylation of olefins in an alkylation feed stream in order to produce a higher yield of alkylate having a higher octane number, a lower acid consumption rate and a lower energy consumption, which process comprises the following steps:
    (a) passing a feed stream comprised of olefins, isoparaffins and normal paraffins through a membrane whereby the olefins are separated from said field stream;
    (b) facilitating transport of said olefins across said membrane by using an isoparaffin sweep stream to form an olefin and isoparaffin mixture;
    (c) passing said mixture from step (b) to an alkylation reactor; and
    (d) reacting within said alkylation reactor said mixture with an alkylation catalyst to form alkylate product.

2. The process of claim 1 wherein said isoparaffin sweep stream comprises isobutane.

3. The process of claim 1 wherein said isoparaffin sweep stream is in the liquid phase.

4. The process of claim 1 wherein said isoparaffin sweep stream is in the vapor phase.

5. The process of claim 1 wherein said feed stream from step (a) passes to a second separation zone to facilitate the separation of said isoparaffins from said normal paraffins.

6. The process of claim 5 wherein said isoparaffins separated from said second separating zone pass into said alkylation reactor and react with said olefins to form said alkylate product.

7. The process of claim 5 wherein said second separation zone comprises a membrane.

8. The process of claim 5 wherein said second separation zone comprises molecular sieves.

9. The process of claim 5 wherein said second separation zone comprises activated carbon.

10. The process of claim 5 wherein said normal paraffin is comprised of normal butane and said isoparaffin is comprised of isobutane.

11. The process of claim 1 wherein said feed stream from step (a) passes to an isomerization unit to facilitate conversion of said normal paraffins to isoparaffins.

12. The process of claim 11 wherein said isoparaffins from said isomerization zone pass into said alkylation reactor and react with said olefins to form said alkylate product.

13. The process of claim 11 wherein greater than 50% of said normal paraffins are converted to isoparaffins within said isomerization unit.

14. The process of claim 1 wherein said membrane in step (a) is impregnated with a silver nitrate solution.

15. The process of claim 1 wherein said isoparaffin in said mixture has 4–8 carbon atoms.

* * * * *

UNITED STATES PATENT OFFICE
CERTIFICATE OF CORRECTION

Patent No. 4,154,770            Dated May 15, 1979

Inventor(s) Richard D. Kaplan

It is certified that error appears in the above-identified patent and that said Letters Patent are hereby corrected as shown below:

| Patent Column | Line | |
|---|---|---|
| 1 | 54 | "molal" should read --molar--. |
| 3 | 49 | "direction" should read --directed--. |
| 5 | 22 | "are" should read --was--. |
| 6 | 20 | "streams" should read --stream--. |
| 7 | 50 | "propane" should read --propane,--. |
| 7 | 57 | "isobutene" should read --isobutane--. |
| 7 | 59 | "propane" should read --propene--. |
| 9 | 35 | "As" should read --An--. |
| 10 | 16 | "field" should read --feed--. |
| 10 | 38 | "separating" should read --separation--. |

Signed and Sealed this

Thirteenth Day of July 1982

[SEAL]

Attest:

Attesting Officer

GERALD J. MOSSINGHOFF

Commissioner of Patents and Trademarks